United States Patent [19]

Collins

[11] 4,317,380
[45] Mar. 2, 1982

[54] DEVICE FOR OBTAINING A SAMPLE OF MOLTEN MATERIAL AND METHODS OF ASSEMBLING COMPONENTS THEREOF

[76] Inventor: William J. Collins, 7005 Madison St., Merrillville, Ind. 46410

[21] Appl. No.: 107,157

[22] Filed: Dec. 26, 1979

[51] Int. Cl.³ .............................................. G01N 1/12
[52] U.S. Cl. .............................. 73/864.56; 73/864.58
[58] Field of Search ................... 73/425.4 R, DIG. 9; 7/167

[56] References Cited

U.S. PATENT DOCUMENTS

| | | | |
|---|---|---|---|
| 2,031,044 | 2/1936 | Jensen et al. | 7/167 |
| 3,369,406 | 2/1968 | Lowdermilk | 73/DIG. 9 |
| 4,002,071 | 1/1977 | Collins | 73/425.4 R |
| 4,002,073 | 1/1977 | Collins | 73/DIG. 9 |
| 4,068,530 | 1/1978 | Collins | 73/425.4 R |
| 4,112,772 | 9/1978 | McDevitt | 73/425.4 |
| 4,206,652 | 6/1980 | Kumbrant | 73/425.4 R |

*Primary Examiner*—S. Clement Swisher
*Attorney, Agent, or Firm*—Charles S. Penfold

[57] ABSTRACT

The invention involves providing a device for sampling a molten material and comprises, among other things, a unique holder or support means which serves to support and hold assembled therein a pair of mating sections which cooperate to define a chamber or mold for receiving a sample of such material for subsequent analysis, and includes modified devices.

32 Claims, 44 Drawing Figures

DEVICE FOR OBTAINING A SAMPLE OF MOLTEN MATERIAL AND METHODS OF ASSEMBLING COMPONENTS THEREOF

SUMMARY OF THE INVENTION

The subject invention includes improvements over many patents issued to the inventor, such as for example those identified by U.S. Pat. Nos.: 4,002,071; 4,002,073; and 4,068,530.

More particularly, the invention or inventions exemplified in the drawings has to do with certain components of the device, such as a support means and means for receiving a sample of molten material which are held assembled and interlocked with the support means in a unique manner, which is presently believed to constitute an improvement or advance over the devices in the above identified patents including all known prior art of record.

The invention or inventions also embodies a unique method of assembling the holder or support means and the receiving means, including modifications thereof.

OBJECTIVES

In view of the foregoing one of the primary objects of the subject invention is to provide a device for the purpose of sampling molten material which includes a subassembly comprising what may be referred to as a holder, support means, cradle or an inner substantially tubular casing which is constructed to receive and hold assembled therein in a unique manner a pair of mating sections which define a chamber or means for receiving a sample of such a material for subsequent analysis.

More particularly, the holder or support means is preferably elongated and comprised of wall structure which is constructed to provide openings for accommodating portions of enlarged extremities or heads of the mating sections for holding the latter assembled in a manner whereby to substantially prevent longitudinal displacement or relative movement between these sections and the support means. This setup or organization provides a subassembly which insures a substantially positive holding of the sections to form a chamber or mold in order to obtain a well formed sample.

A significant objective of the invention is to provide an outer elongated housing for the subassembly and means for holding the latter therein which preferably includes a mass or masses of insulating material or refractory cement which embraces or engages frontal portions or extremities of the subassembly and/or housing whereby to assist in holding the subassembly in place and in protecting such frontal portions when the device is being utilized to obtain a sample from the molten material.

A specific object of the invention is to provide a device in which the outer housing and the subassembly confined therein are preferably of rectangular cross-dimensions or noncircular in cross-sections and a mass of the insulating material or cement, as alluded to above, is preferably formed to provide what may be termed a tapered or forwardly extending formation whereby to facilitate entry of the device into a supply of molten material and thereby minimize splash or repulsion.

Another specific objective is to provide the receiving means or mold with tublar means through which the molten material is initially received for flow into the mold or chamber and the mass or masses of insulating material or cement additionally serve to hold the tubular means in relation to the mold and housing.

A further specific object is to provide the housing with an external jacket or sleeve, preferably of a metallic sheet material, for protecting the housing when the device is utilized and during shipment prior to use.

Also, a specific object is to provide an assortment of non-metallic tubular means or tubes for receiving the molten material for flow in the chamber of the mold.

The invention also contemplates a unique method of assembling the mating sections and support means and novel structure affording a setup whereby to facilitate connection of the device to a wand or lance so that the device can be readily manipulated into a supply of molten material.

More particularly, the lance or wand for facilitating manipulation of the device is considered to embody improved principles of design and construction and preferably includes an elongated tubular member having a rear extremity provided with a detachable handle and a curved or angled front extremity provided with means whereby any one of a number of different adapters or elements can be readily detachably connected thereto for detachable connection with any one of a number of different types or forms of devices for sampling molten material or an extremely hot liquid.

Particularly significant objectives reside in providing devices which offer advantages whereby the components thereof lend themselves to manufacture and assembly on a production basis and efficiency in obtaining samples of molten material.

Additional objectives and advantages of the invention or inventions will become apparent after the description hereinafter set forth is considered in conjunction with the drawings annexed hereto.

DRAWINGS

In the drawings:

FIGS. 1, 2, 3, 4, 5 and 6 are directed to what may be referred to as a preferred device embodying the invention or inventions;

FIGS. 9, 10 and 11 illustrate what may be identified as a second embodiment or modification of the invention or inventions;

FIGS. 17, 18 and 19 depict a third modification of the invention or inventions;

FIGS. 20, 21, 22, 23, 24, 25, 26, 27 and 28 disclose a fourth modified structure;

FIGS. 32, 33 and 34 are directed to a fifth embodiment of the invention or inventions;

FIG. 40 shows the adapter of FIG. 39 connected with a sampler device;

DESCRIPTION

Referring first to the device or structure illustrated in FIGS. 1, 2, 3, 4, 5 and 6 numeral 1 generally designates one preferred embodiment of the invention or inventions. This device is preferably designed and constructed to provide an elongated outer housing 2 and a subassembly confined therein and comprising what may be referred to as a holder, support means, cradle or tubular structure generally designated 3 which serves to hold a pair of mating sections 4 and 5 in an assembled relation with respect to one another and the support means. The mating sections may be constructed as desired but are preferably made of molded powdered metal and comprise enlargements or head portions 6 provided with internal recesses or cavities to form a chamber 7 for receiving a sample of a molten material from a source or supply thereof. These sections are also preferably constructed to form reduced channel portions which provide a tubular formation 8 (see FIG. 25) for accommodating a rear extremity of a tubular means or tube 9 of quartz, Pyrex or equivalent material, for initially receiving such molten material for flow into the chamber 7 for eventual solidification.

One of the significant objectives of the subject invention is to provide a unique subassembly comprising the holder or support means 3 and the means for receiving the molten material.

Figures 1, 2, 3, 5, 6, 7, 9, 10, 14, 15, 16:
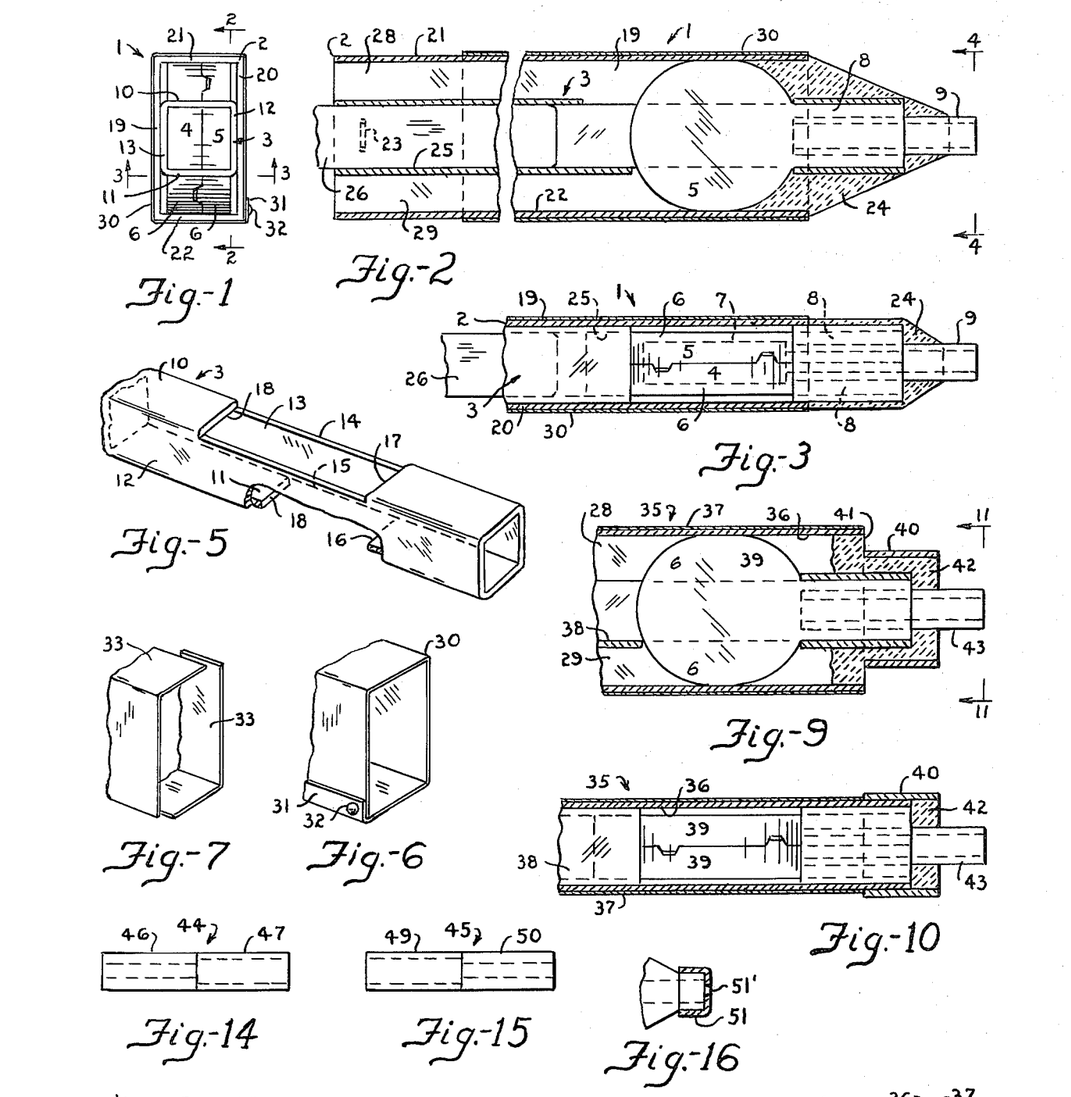
FIG. 1 is a rear elevational side view of the device shown in FIG. 2.
FIG. 2 is a vertical section taken substantially on line 2—2 of FIG. 1.
FIG. 3 is a transverse section taken substantially on line 3—3 of FIG. 1.
FIG. 5 is a partial perspective view of an internal component or holder of the device shown in FIGS. 1 through 4.
FIG. 6 is a partial perspective view of a sleeve embracing the device shown in FIGS. 1 and 2.
FIG. 7 is a partial perspective view of a modified form of sleeve structure that can be utilized in lieu of the sleeve of FIG. 6.
FIG. 9 is a partial vertical section of the aforesaid second modification.
FIG. 10 is a bottom view of the structure shown in FIG. 9.
FIGS. 14 and 15 respectively illustrate different forms of tubular means which can be utilized in lieu of the tubes shown in FIGS. 2 and 9.
FIG. 16 is a partial side view of a front end of a device showing a cap which may be affixed to any of the tubes of the devices illustrated.
Figure 4:
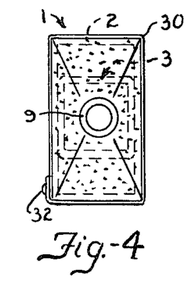
FIG. 4 is a front elevation view of the device looking in the direction of the arrows 4—4 of FIG. 2.

More particularly in this regard the holder is preferably of a generally elongated tubular construction, as best shown in FIG. 5, and includes a pair of upper and lower planar parallel walls 10 and 11 and a pair of planar parallel side walls 12 and 13. The upper wall 10 is provided with an elongated opening or cutout 14 and the lower wall 11 with an elongated opening or cutout 15 which is of a length somewhat shorter than the opening 14 so that a fore marginal edge 16 thereof is located directly below a fore marginal edge 17 of the opening 14. In other words, the fore marginal edges 16 and 17 are preferably disposed the same distance away from the front end of the holder 3 and so that a rear marginal end 18 of the opening 14 is disposed a greater distance away from the front end of the holder. It should be noted that the sizes and locations of the upper and lower openings 14 and 15 are predetermined and preferably disposed in the front extremity of the holder, the purpose of which is to facilitate assembly or entry of the mating sections as a unit into the holder. The method of assembling the components is accomplished by holding the sections together and inserting them forwardly as a unit in an inclined position so that the tubular formation 8 formed by the channel portions of the sections will enter the upper opening 14 and into the fore extremity of the holder until portions of the enlargements 6 find their way into the opposed openings 14 and 15 whereby to substantially provide an interlocking relationship between the support means and sections. More particularly, portions of the enlargements project outwardly through the aforesaid openings and laterally of the holder and are more or less held in engagement with edges 16 and 18 and more or less in engagement with the edge 17 and the walls of the holder serve to snugly engage the mating sections to hold them in an intimate relationship.

The elongated outer housing 2, above referred to, is of tubular construction and comprises a pair of parallel planar side walls 19 and 20 and a pair of upper and lower parallel planar walls 21 and 22, the width of the latter being less than that of the side walls, thereby providing a housing which is substantially rectangular in cross-section as compared to the holder 3 which is substantially square in cross-section. These components may be constructed of any material suitable for the purpose but are preferably made of a cellulosic material such as pasteboard and their lineal and cross-dimensions are predetermined.

The holder 3 is preferably made somewhat longer than the housing so that when the subassembly or unit comprising the holder and mating sections, is correctly inserted into the housing inner opposed surfaces of the walls of the housing will engage the walls of the holder and thereby augment or assist in holding the mating sections in a pressured assembled relationship, as well as assist in holding the holder and housing assembled. The holder is disposed in a center or axial position in the outer housing and so that a front extremity of the holder and tubular formation 8 extend a predetermined distance forwardly of the housing.

The rear extremity of the holder may be anchored or fixedly secured in the rear extremity of the housing by any fastening means suitable for the purpose, such as by a pair of staples of which one identified by numeral 23 is depicted in FIG. 2.

The tubular means 9, as referred to above, has an inner extremity which is disposed in the tubular formation 8 and it has a front extremity which extends a predetermined distance forwardly of the front ends of the tubular formation and holder 3 and a mass or masses of insulating material or refractory cement 24 is pressed into the front extremity of housing about the tubular formation and assist in holding the mating sections and holder assembled with respect to one another and the outer housing and thereby protect the front extremity of the device when it is utilized to penetrate a mass or supply of material to obtain a sample therefrom. The mass of insulating material is preferably shaped to provide a generally tapered, pointed or nose-like formation, as shown, whereby to facilitate penetration of the device into the supply and alleviate or reduce splash or repulsion. The fact that the device is multi-sided or non-circular in cross-section also serves to promote its insertion in the molten material and thereby reduce splash.

Figures 35, 36, 37, 38:
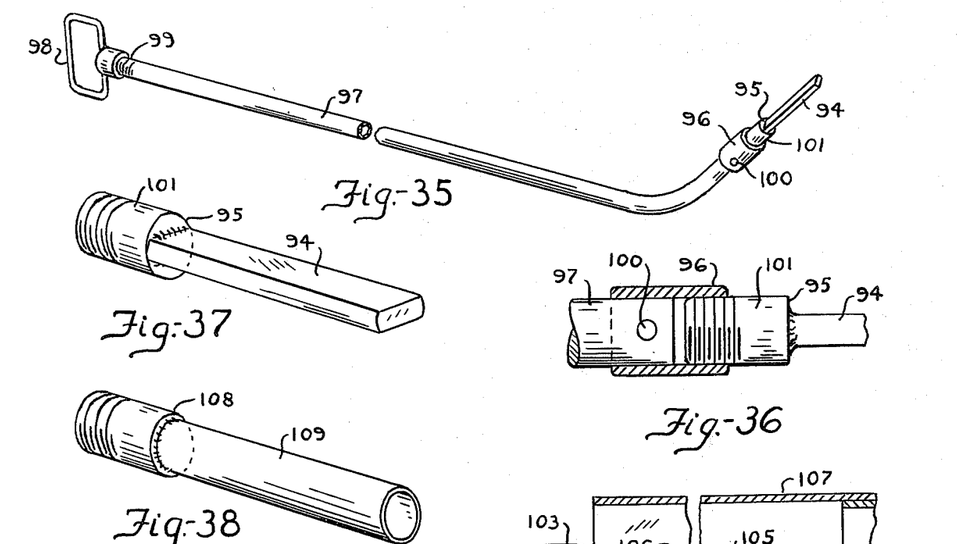
FIG. 35 is a perspective view of a lance or wand which is so designed and constructed that it can be utilized for detachable connection with any one of several different forms of sampling devices.
FIG. 36 is a partial sectional view of fitting carried by a front extremity of the lance shown in FIG. 35 and an adapter or connection means which is detachably connectible with the fitting.
FIG. 37 is a perspective view of the adapter shown in FIG. 36.
FIGS. 38 and 39 are perspective views of different forms of adapters.
Figure 39:
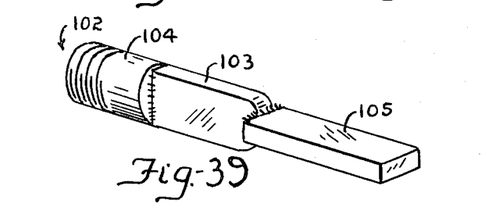

It should be observed that the rear extremity of the support means is centered in the outer housing and provides a formation 25 which serves to detachably frictionally slidably engage or accommodate an adapter 26 adapted to be carried by a lance or wand 97, the latter being shown in FIG. 35. Obviously, adapters of different shapes can be utilized as depicted in FIGS. 37, 38 and 39. Due to the difference in cross-dimensions between the outer housing and holder, these two components provide an upper formation 28 and a lower formation 29 on opposite sides of the center formation 25, the arrangement being such, that the adapter 26 on a lance 97 is adapted to be inserted into the formation 25 but an adapter of larger cross-dimensions can be inserted into either of the formations 28 and 29 whereby to facilitate manipulation of the device to obtain a sample of molten material. Attention is directed to the fact that any one or all of the aforesaid rear formations, including the other rear formations hereinafter described, allow for venting of any gases which flow outwardly from between the mating sections of the receiving means when the sample of molten material in filling the chamber formed by the sections.

Figure 8:
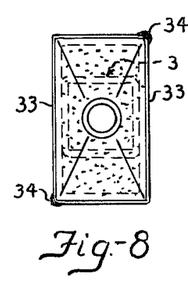
FIG. 8 is a front elevational view of structure similar to that shown in FIG. 4, depicting a mode of securing the sectional structure of FIG. 7 together.
Figure 11:
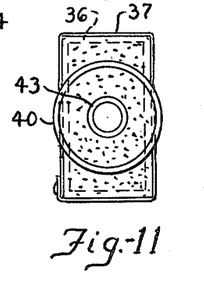
FIG. 11 is a front elevational view looking in the direction of the arrows in FIG. 9.
Figure 12:
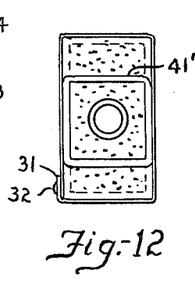
FIG. 12 is a view similar to FIG. 11, except for a different form of a frontal component.
Figure 13:
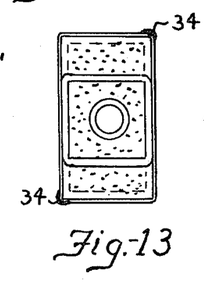
FIG. 13 is a view similar to FIG. 12 showing the sleeve structure of FIG. 8.

The outer housing 2 is preferably protected by a metal sleeve or sheath 30 which embraces the housing and which is secured thereto by providing the sleeve with a flange 31 which is affixed to a wall of the sleeve by fastening means, such as by rivets 32, depicted in FIGS. 1, 4, 6, 11 and 12 or if, so desired, the sleeve may be comprised of a pair of corresponding L-shaped sheet metal members 33 which are preferably assembled about the housing by a pair of diagonally disposed longitudinal welds 34 as shown in FIGS. 8 and 13. These sleeves may extend appreciably throughout the front extremity of the housing as depicted in FIG. 2 or they can be constructed to extend throughout the full length of the housing.

A second embodiment or modification of the invention is exemplified in FIGS. 9, 10 and 11 and is generally designated 35. More particularly, it preferably comprises an outer elongated housing 36 protected by a sleeve 37; an inner elongated holder or support means 38 and a receiving means formed by mating sections 39 which respectively substantially correspond to the holder and mating sections described above. It should be noted that the front extremity of the holder 38 does not extend forwardly beyond the outer housing to the same extent as that shown in FIG. 2. An annular member or relatively short cylindrical member 40 abuts the front end of the housing and surrounds the extended portion of the holder and a mass of insulating material or refractory cement 41 is packed about the extended portion and into the housing and a mass 42 is placed in the member 40, and about the extended portion and engages the mass 41. The mass 42 also extends forwardly of the extended portion of the holder and about a tubular means or tube 43 so that a fore extremity of the latter is exposed for initially receiving a sample of molten material. These masses of cement serve to protect the assembled front extremity of the device 35.

FIG. 12 is a front end elevational view of a modified structure which is quite similar to FIG. 11, except that a squared member 41' is utilized in lieu of the annular member 41 of FIG. 11; and FIG. 13 is similar to FIG. 12 except that a two part sleeve structure like that in FIGS. 7 and 8 is employed which are preferably fastened together by the welds 34.

FIGS. 14 and 15 show different forms of tubular means or tubular structures generally designated 44 and 45.

Figures 20, 21, 22, 23, 24, 25, 31:
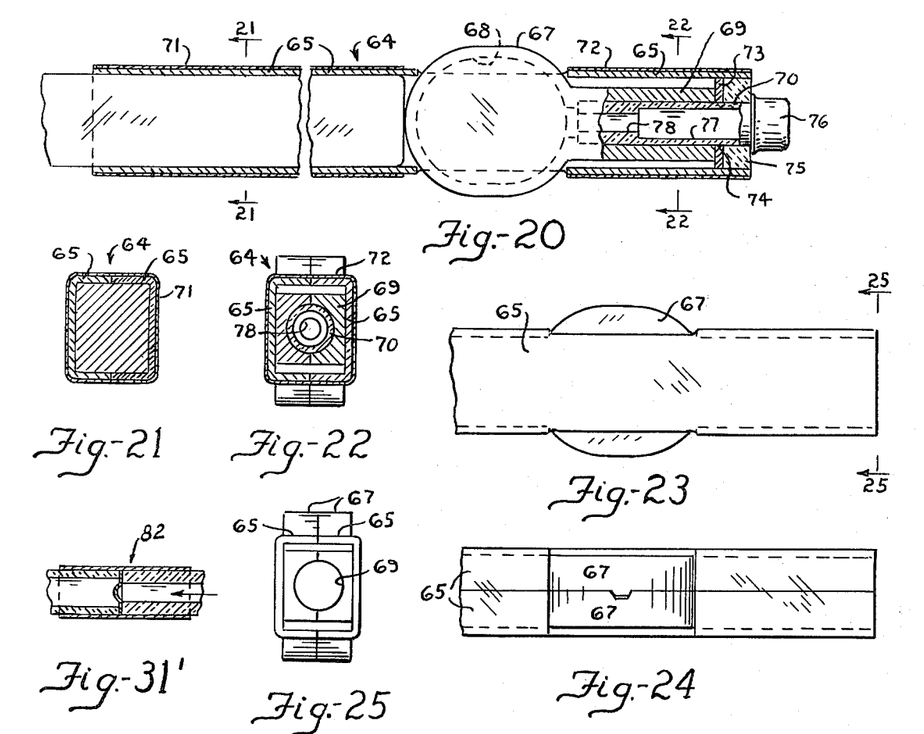
FIG. 20 is a vertical section of the device.
FIG. 21 is a transverse section taken substantially on line 21—21 of FIG. 20.
FIG. 22 is a transverse section taken substantially on line 21—21 of FIG. 20.
FIG. 23 depicts a subassembly comprising means for receiving a sample of molten material and a holder or support means therefor, with portions broken away.
FIG. 24 is a top view of the structure of FIG. 23.
FIG. 25 is a front elevation view of FIG. 23 looking in the direction of the arrows 25—25.
FIGS. 29, 30, 31, and 31' are variations of the tubular means shown in FIGS. 2, 9, 20 and 28, including those of FIGS. 14 and 15.
Figure 29:
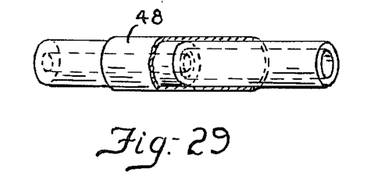

The tubular means or structure of FIG. 14 comprises a pair of tubes 46 and 47 of quartz, Pyrex or equivalent material which are held together in an axial abutting relation by any suitable fastening means, such as by a wrapping material or sleeve 48 as shown in FIGS. 29 and 31. These tubes preferably have the same outside cross-dimensions but tube 47, which is adapted to initially receive molten material, has a larger predetermined internal cross-dimension or diameter than that of tube 46 in order to facilitate flow of the material through the latter.

The tubular means 47 depicted in FIG. 15 substantially corresponds to the tubular means of FIG. 14 and comprises a pair of tubes 49 and 50, except that the latter which is adapted to initially receive the molten material has an internal cross-dimension or diameter which is less than that of tube 49.

The tubular means 46 and 47 may be utilized in lieu of the tubular means 9 and 43 above referred to, the uses depending on the character and/or liquidity of the supply of material to be sampled. It is to be understood that the cross-dimensions and the lengths of all of various tubular means described above, including those shown in FIGS. 17, 18, 19, 20, 28, 29, 30, 31, 31' and 32 are preferably predetermined.

FIG. 16 is a partial elevational view and is presented to show that a cap 51, if so desired, may be connected to the fore end of any of the tubular means whereby to prevent, for example, entry of any foreign matter when the tubular means of any of the devices is being inserted into a supply of molten material. This cap is provided with an aperture 51' whereby to facilitate disintegration of the cap. The cap or closure disintegrates in the supply after it has served its purpose.

Figure 17:
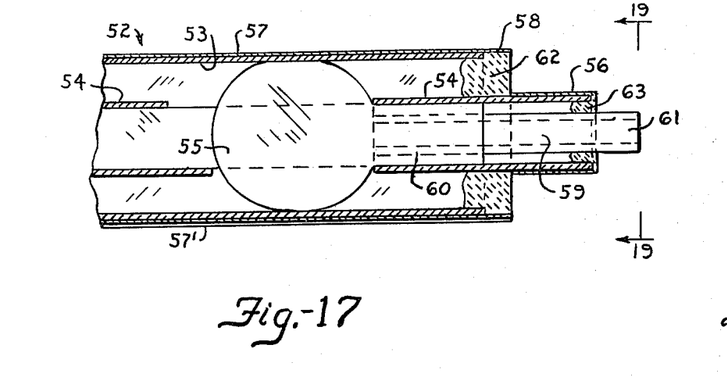
FIG. 17 is a vertical section of this third modified device which is different in certain respects from the device of FIG. 2.
Figure 18:
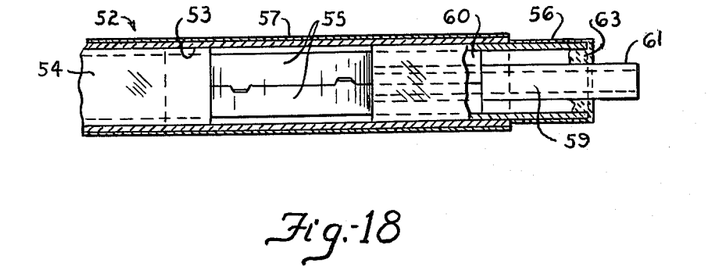
FIG. 18 is a bottom view of FIG. 17, with portions in section.
Figure 19:
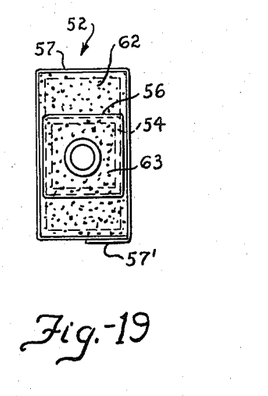
FIG. 19 is a front elevational view of FIG. 17 looking in the direction of the arrows 19—19.

A third modification or device embodying the invention or inventions is disclosed in FIGS. 17, 18 and 19 and is generally designated 52. More particularly, this modification is quite similar to the embodiment shown in FIGS. 1, 2 and 3 and comprises an elongated outer housing 53, an inner holder or support means 54 secured in the housing with a fore extremity extending forwardly of the front end of the housing, a receiving means comprising a pair of mating sections 55 secured in an assembled relation in the holder so that external upper and lower portions of enlargements of the sections extend through opposed openings in the holder and intimately engage inner surfaces of the upper and lower walls of the housing and side surfaces of the enlarged portions intimately engage opposed inner surfaces of the side walls of the holder whereby to assist in holding the sections in relation to the housing and holder and the latter in relation to the housing as substantially described above with respect to the preferred embodiment of the invention or inventions. In other words, there are predetermined frictional holding relationships between the aforementioned components, in addition to the holding action of a fastening means, such as the staples 23 as shown in FIG. 2.

It should be noted that the front extremity of the holder 54 forwardly of the receiving means is somewhat longer than the front extremity of the holder 3 in FIG. 2 and a portion thereof extends forwardly of the housing. A sleeve 56 constructed of any material suitable for the purpose, such as metal or pasteboard is fitted on the extended portion of the holder. An elongated sleeve or sheath 57 of suitable material is fitted about the outer housing and a frontal portion 58 is preferably extended a predetermined distance forwardly thereof as shown in FIG. 17. This sleeve has an overlap 57' of a sufficient size which does not necessarily require the use of rivets or welds.

A tubular means or tube 59 has an inner extremity secured in a tubular formation 60 formed by channels of the mating sections and a fore extremity 61 extends a predetermined distance forwardly of the outer housing and the extended portion of the holder 54 for entry into a supply of molten material.

A mass 62 of insulating material or refractory cement is disposed at the front extremity of the device 52 in the frontal area of the outer housing 53 and sleeve 58 and about the front extremity of the holder and a mass 63 is disposed in the holder 54 and about the tube 61 and against the frontal edges of the holder and sleeve 56, all for the purposes of stabilizing the operative positions of the components and protecting them sufficiently to permit an operator to obtain a satisfactory sample from a supply of molten material as well as protection during shipment prior to use.

Figure 26:
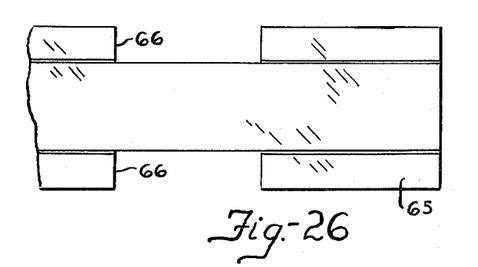
FIG. 26 discloses a partial surface development of one of the members of the holder.
Figure 27:
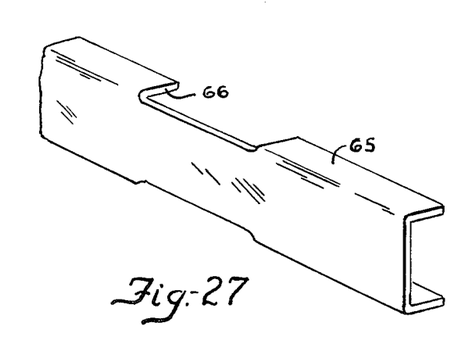
FIG. 27 is a partial perspective view of one of a pair of corresponding members which when correctly assembled provide a holder or support for the receiving means.

A fourth embodiment or structure of the invention or inventions are illustrated in FIGS. 20, 21, 22, 23, 24, 25, 26, 27 and 28. This particular structure primarily differs from the structures described above by eliminating an outer elongated pasteboard housing, and is generally designated 64 and preferably comprises an elongated tubular holder or support means which is preferably rectangular or square in cross-section and is formed by a pair of generally corresponding channel members 65 as best depicted in FIGS. 25 and 27. Each of the members 65 is preferably constructed from a flat or planar elongated rectangular piece of pasteboard which is interrupted at its sides by cut-outs or notches 66 as best depicted in FIG. 26.

This fourth embodiment, modification or device also comprises a pair of mating sections 67 having enlargements or head portions and reduced channel portions which when correctly assembled provide a chamber 68 and a tubular formation 69, the latter of which receives an inner extremity of tubular means or tube 70 which serves to initially receive a sample of molten material.

The mating sections and channel members of the holder or support means can be readily assembled by preferably manually holding the mating sections 67 together and then placing the channel members 65 about the sections so that portions of the enlargements of the sections will extend outwardly or laterally through side openings formed by the notches 66 to interlock the component as clearly illustrated. It should be noted that the openings formed by the notches are of a corresponding size as compared to the different sized openings in the holder of FIGS. 2, 9 and 17. A pair of external sleeves 71 and 72 are preferably fitted about the channel members 65 and relative to the mating sections assembled therein for holding them together and for protective purposes as shown. If so desired, a sleeve can be constructed from a single piece of sheet material which can be provided with cut-outs or openings which are of size sufficient to permit placement of this material about the holder, allowing clearance for portions of the enlargements or heads of the sections.

The receiving means formed by the mating sections 67 is secured in the front extremity of the holder and a partition 73 is disposed in and inset in the holder for engaging the front end of the tubular formation 69 and is provided with an aperture 74 through which the tube 70 extends. A front end of the tube extends forwardly of the holder and a mass of insulating material or cement 75 is placed in the front extremity of the holder, about the tube, and against the partition whereby to prevent rear flow of any molten material into the tubular formation and or space about this formation. The partition also assists in this regard. In certain instances, depending on the liquidity and/or mode of sampling, a cap 76 may be secured to the entrance end of the tube for substantially the same purpose as the cap 51 and may contain a means for conditioning the sample as it flows into the tube 70.

It should be noted that the rear extremity of the holder 65 serves to detachably accommodate a fore extremity of a lance or an adapter connected thereto.

The tube 70 is preferably constructed in one piece as shown in FIG. 20 and provided with a front cylindrical entrance opening 77 of a predetermined cross-dimension and a rear opening 78 having a cross-dimension which is somewhat smaller than the opening 77. The tube shown in FIG. 28 substantially corresponds to the tube 70 but is somewhat longer.

The tubular means or tube disclosed in FIGS. 29 and 31 are quite similar to the tubular means 44 and 45 in FIGS. 14 and 15. More specifically, in this regard FIG. 29 shows the tubes 46 and 47 of FIG. 14 secured together by the fastening means 48 as alluded to above.

Figure 28:
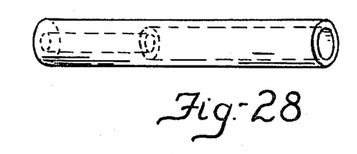
FIG. 28 is a pictorial view of a tubular means which is longer than the one shown in FIG. 20.
Figure 30:
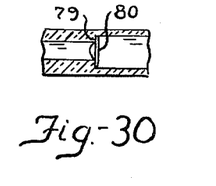
Figure 31:
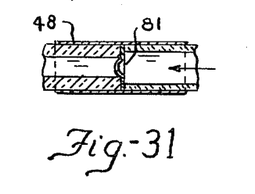

FIG. 30 is a partial section showing the tube 70 of FIG. 20 or the tube of FIG. 28 being provided with a seat 79 and a means 80 which is disposed on or in relation thereto for conditioning or deoxidizing molten material as it flows from the larger opening or passage into the smaller opening of the tube.

FIG. 31 is similar to FIG. 29 and shows a conditioning means 81 which is held between inner ends of tubes such as 46 and 47 of FIG. 14, with a fastening means, such as 48, for holding the tubes and conditioning means assembled.

FIGS. 31' discloses a tubular means generally designated 82 which is substantially a reversal of the tubular means of FIG. 31 and shows a pair of tubes corresponding to those of FIG. 15, plus a conditioning means and a fastening means like FIG. 31.

The tubular means of FIGS. 14, 15, 28, 29, 30, 31 and 31' and are obviously usable with any of the sampling devices disclosed in this application. It should be noted that these tubular means are also disclosed in Applicant's application Ser. No. 075,941 filed Sept. 17, 1979.

In FIGS. 32, 33, 34 and 41 there is illustrated what may be referred to as a fifth modified structure or device which is generally designated 80 comprising an elongated outer housing 81 within which a subassembly comprising an elongated casing 82 containing a pair of mating sections 83 (one shown), a partition 84, a tube 85, a mass of cement or insulating material 86, and a cap 87.

Figure 32:
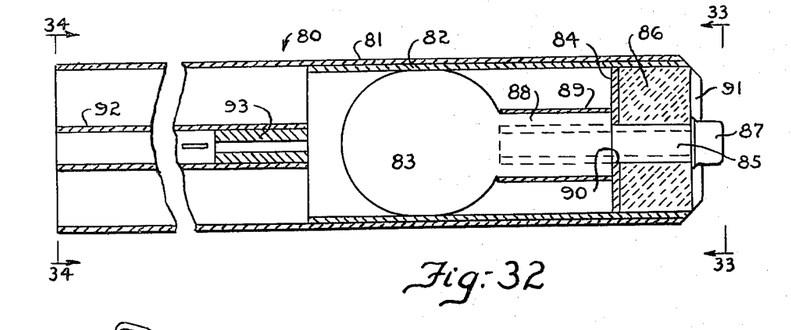
FIG. 32 is a vertical section taken through a device.
Figure 33:
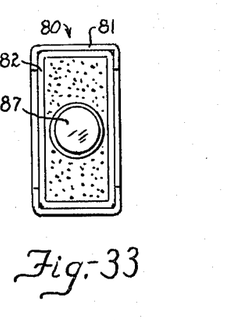
FIG. 33 is a front elevational view of FIG. 32 looking in the direction of the arrows 33—33.
Figure 34:
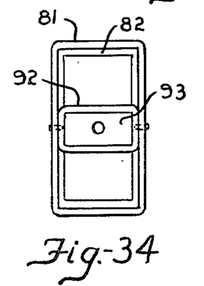
FIG. 34 is a rear elevation view of FIGS. 32 looking in the direction of the arrows 34—34.

The mating section 83 preferably correspond to those, above referred to, which form a chamber for receiving a sample of molten material and a tubular formation 88 or opening in which a rear extremity of the tube 85 is held therein by a fastening means, such as a wrap or sleeve 89 and a front extremity of this tube extends through an aperture 90 provided in the partition. This partition is inset from the front marginal end edge of the casing and the mass of cement 86 is packed into the front extremity of this casing against the partition 84 and about the tube 85. The frontal face of the mass is preferably generally flush with the end edge of the casing, so that extended side or wing portions 91 (one shown) of the outer housing 81 extend forwardly of the casing and mass of cement for protective purposes, and the cap 87 is interposed between these wing portions as depicted in FIG. 32.

The subassembly comprising the casing and mating sections is substantially held against forward movement in the housing by the partition and mass of cement and rear movement is substantially prevented by a tubular formation or sleeve 92 which is fixedly secured in a rear extremity of the housing against the casing 82. Any fastening suitable for the purpose may be utilized to anchor the rear formation 92 in position, such as for example, by staples as shown. A tubular element 93 is secured in the formation 92 against the holder and serves as a stop or abutment means for limiting inward movement of an adapter or lance and thereby prevent engagement with the mating sections. This rear formation, for example, serves to detachably accommodate the front extremity 94 of the adapter 95 shown in FIG. 37. This adapter is preferably detachably connectible with a fitting 96 carried by a curved front extremity of the lance or wand 97. This lance is preferably tubular and of a sufficient length to permit an operator to safely insert the device into a supply of molten material to obtain a sample therefrom. The lance is provided with a detachable handle 98 which is preferably threadably connected to a threaded portion 99 of the lance and the fitting 96 is preferably of tubular construction and connected to the lance by a cross-pin or element 100. This fitting is preferably internally threaded for detachable connection with an external threaded portion 101 of the adapter 95 as shown in FIGS. 35 and 36.

Figure 41:
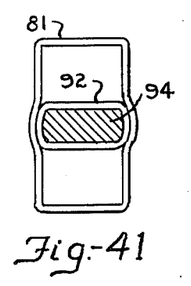
FIG. 41 is a rear elevational view of FIGS. 34 and 40 showing what occurs when an adapter such as those depicted in FIGS. 37 and 39 are selectively employed.

The entering part or extremity 94 of the adapter 95 is adapted for manual insertion into the formation 92 and the internal cross-dimensions of this formation and the cross-dimensions of the part 94 are preferably such that a satisfactory frictional fit or connection is achieved to expand or enlarge the formation and/or side walls of the housing as exemplified in FIG. 41. The part 94 of the adapter is preferably welded to the threaded portion 101 of the adapter 94.

Figure 42:
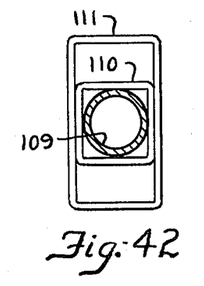
FIG. 42 is a rear elevational view of a device showing the adapter of FIG. 38 connected thereto.

In FIG. 38 there is disclosed a different adapter 108 which is similar to the adapter 95 but differs therefrom by having a cylindrical entering part 109 which is suitable for insertion into a rear tubular formation 110 which is substantially square in cross-section for accommodating the part 109 as depicted in FIG. 42. The formation 110 is secured in an outer tubular housing 111.

FIG. 39 depicts a modified adapter generally designated 102 which has a portion 103 which is welded to an externally threaded portion 104 and an entering part 105 welded to the portion 103 for disposition in a plane perpendicular thereto. The entering part 105 is adapted for insertion in a tubular formation 106 secured in a rear extremity of an outer housing 107 of a device which more or less corresponds to the device 80. The portion 103 serves to engage the formation 106 and thereby limit the travel distance of the entering part into the formation so that the latter cannot engage and dislocate the mating sections.

Figure 43:
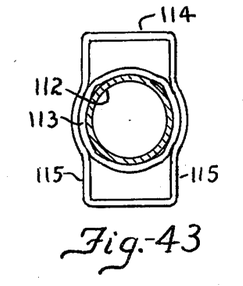
FIG. 43 is a view showing an adapter of a larger cross-sectional dimension connected to a sampling device.

With respect to FIG. 43 it will be evident that an adapter may be provided with a cylindrical entering part 112 which has a cross-section appreciably greater than the entering part 109 of FIG. 42 for reception in a rear tubular formation 113 in an outer housing 114 in a manner whereby the formation, and side walls 115 of the housing will expand somewhat similar to the structure of FIG. 41 for holding purposes.

In view of the foregoing it should be manifest that the various modifications or embodiments of the invention or inventions offer advantages with respect to the design and construction of the various components. More particularly, provision is made whereby the mold sections can be assembled by either of two methods to two different forms of holders or support means, and that the devices are preferably multi-sided or substantially rectangular in cross-dimension in order to minimize splash or repulsion when the devices are utilized in obtaining a sample from a supply of molten material or liquid.

The invention also provides for protecting the devices and particularly the front extremities of certain of the components and providing the device with different forms of rear formations for engaging or accommodating different forms of adapters or lances and thereby render the devices more versatile for use.

Having thus described my invention or inventions, it is obvious that various modifications or additions to those described may be made in the same without departing from the spirit of the invention and, therefore, I do not wish to be understood as limiting myself to the exact forms, constructions, arrangements, and combinations of the components herein shown and described.

I claim:

1. A holder for use with a pair of elongated mating sections which form a head provided with a chamber for receiving a molten material and a reduced tubular formation through which such a material may be caused to flow into the chamber, said holder comprising walls forming an elongated substantially tubular structure provided with opposed openings for receiving portions of such a head whereby to assist in holding such a pair of sections assembled lengthwise in said holder.

2. The holder defined in claim 1, in which one of said openings is larger than the other whereby to facilitate entry of the sections into the holder through the larger opening.

3. The holder defined in claim 1, in which said wall structure is constructed of a cellulosic material and comprises a pair of channel members provided with notches which cooperate to form the openings when these members are assembled.

4. A subassembly comprising an elongated holder provided with opposed openings intermediate its length, and an elongated device extending lengthwise in said holder for receiving a sample of molten material and having portions disposed in said openings whereby to establish an inter connection between said holder and device.

5. The subassembly defined in claim 4, including an elongated housing disposed about said holder throughout the major portion of its length, said device also has portions extending longitudinally forward of said housing, and a mass of cement is disposed in said housing and about said extending portions of said device.

6. The subassembly defined in claim 4, including a housing disposed about said holder, said device also has portions extending longitudinally forward of said housing, a mass of cement is disposed in said housing about said extending portions of said device, and a split sleeve is disposed about the housing for protecting the latter and has portions secured together by fastening means.

7. The subassembly defined in claim 4, including a housing disposed about said holder, and a pair of L-shaped members secured together about said housing.

8. The subassembly defined in claim 4, in which a rear extremity of said holder is multi-sided and expandible and serves to detachably accommodate a fore cylindrical entering part of a lance.

9. Structure for the purpose described comprising an inner elongated substantially tubular holder provided with a pair of opposed openings and a front extremity, a pair of mating sections forming a chamber and having portions disposed in said holder and said openings, tubular means having an inner extremity connected to said chamber and an entrance end extending longitudinally forward of said holder for initially receiving a sample of molten material for flow into said chamber, and means disposed in said front extremity and surrounding a portion of said tubular means for stabilizing the latter.

10. A device for obtaining a sample of molten material, said device comprising an elongated tubular structure having a fore extremity and a pair of opposed openings disposed intermediate its length, a pair of mating sections forming a chamber and having portions disposed in said structure and exposed portions extending through said openings and laterally of said structure, tubular means having an inner end connected to said chamber and a front entrance end for initially receiving molten material for flow into said chamber whereby to obtain a sample thereof, means protecting said tubular means and said fore extremity, and means surrounding and protecting at least portions of said tubular structure located between said exposed portions of said mating sections and said entrance end of said tubular means.

11. Structure for the purpose described comprising an elongated outer housing having a fore end, an inner elongated substantially tubular holder provided with a pair of opposed openings and a fore end extending forwardly of the fore end of said housing, a pair of mating sections forming a chamber and having portions disposed in said holder and said openings, tubular means having an inner extremity connected to said chamber and a fore end extending forwardly of said fore end of said holder for initially receiving a sample of molten material for flow into said chamber, and means stabilizing the positions of the fore ends of said holder, tubular means and housing.

12. The structure defined in claim 11, in which said last-mentioned means comprises a mass of cement which is generally tapered.

13. The structure defined in claim 11, in which said last-mentioned means comprises a mass of cement and the portion thereof which stabilizes the fore end of said tubular means is substantially cylindrical.

14. A device for obtaining a sample of molten material, said device comprising a pair of notched channel members which form an elongated tubular structure having a fore extremity and a pair of opposed openings disposed intermediate its length, a pair of mating sections forming a chamber and having portions disposed in said structure and exposed portions extending into said openings and laterally of said structure, tubular means having an inner end connected to said chamber and a front entrance end for initially receiving molten material for flow into said chamber whereby to obtain a sample thereof, means protecting said tubular means adjacent its front end, and means surrounding at least portions of said tubular structure located between said exposed portions of said mating sections and said entrance end of said tubular means for holding said mating sections together and said channel members assembled about said sections.

15. A device for the purpose described comprising an elongated tubular outer housing, an inner casing secured in a front extremity of said housing, an elongated mold secured in said casing and comprising a pair of mating sections forming a chamber and a tubular formation, a partition disposed in said casing in an abutting relation to said formation, tubular means having an inner extremity secured in said tubular formation and an outer extremity for initially receiving a sample of molten material for flow into said chamber, a mass of cement disposed in said casing against said partition and about said outer extremity, means disposed in a rear extremity of said housing for slidably engaging a lance, and means carried by said disposed means for limiting the extent of such slidable engagement.

16. A device for the purpose described comprising an elongated outer housing, an elongated casing secured in said housing and having a fore extremity extending forwardly of said outer housing, a mold secured in said casing and having a chamber and a tubular formation, tubular means having an inner extremity disposed in said tubular formation and an outer extremity for initially receiving a sample of molten material for flow into said chamber, a mass of cement disposed in said housing about said casing, and cement disposed in casing about said tubular means.

17. The device defined in claim 16, including sleeve means secured about said housing.

18. The device defined in claim 16, including a sleeve secured about said fore extremity of said casing.

19. An elongated holder for a mold having an enlargement and a tubular formation, said holder being multi-sided to form a pair of opposed walls which are respectively provided with opposed openings for receiving such an enlargement and such a tubular formation is substantially concealed within the confines of said holder.

20. A device for the purpose described comprising an elongated tubular outer housing having a front extremity, an elongated inner tubular casing secured in said housing and having a fore extremity extending a predetermined distance forwardly of said front extremity, a mold secured in said casing provided with a chamber for receiving a sample of molten material, tubular means having an inner end communicating with said chamber and a fore extremity extending forwardly of said casing for initially receiving such a material for flow into said chamber, a tubular member surrounding portions of said fore extremities, and cement disposed in said housing and member about said portions of said fore extremities.

21. A method of assembling an elongated tubular structure provided with a pair of opposed openings intermediate its length and an elongated mold having an enlargement forming a chamber for receiving a sample of molten material and a tubular formation for accommodating a tubular means through which such a material may be caused to flow into the chamber which comprises; manually inserting the tubular formation into the tubular structure via one of the openings and so that the enlargement will be disposed in both openings whereby to limit relative longitudinal movement between said tubular structure and mold.

22. A method of assembling a pair of elongated notched channel members and an elongated mold having an enlargement forming a chamber for receiving a sample of molten material and a tubular formation through which such a material may be caused to flow into the chamber which comprises: manually placing the members about the mold so that the enlargement and the tubular formation both extend between certain portions of the members and the enlargement also extends into the notches whereby to limit relative longitudinal movement between said members and mold.

23. The method defined in claim 22, including the placement of sleeves about said channel members at locations on opposite sides of said enlargement for holding said members about said mold.

24. An elongated member having a rear externally threaded extremity for detachable connection with a lance and a front extremity, and a tube having an inner end welded to said front extremity, and an outer extremity for detachable sliding connection throughout the major portion of its length with a rear formation centrally disposed in an elongated housing of a device for obtaining a sample of molten material.

25. An elongated member having a rear externally threaded extremity for detachable connection with a lance and a front extremity, an entering part for detachable sliding connection throughout the major portion of its length with a formation centrally disposed in an elongated housing of a molten material sampler, and elongated means fixedly secured between said front extremity and said entering part and having a front end serving to predetermine the extent of the connection between said part and such a formation.

26. An elongated device having a front extremity provided with means for receiving a sample of molten material and a rear extremity provided with an inner reduced central tubular formation having a cross-dimension appreciably less than the cross-dimension of said rear extremity for slidable connection throughout the major portion of its length with an entering part of a lance, and stop means secured in the fore part of said formation for limiting the extent of the insertion of said part in said formation.

27. In combination: an elongated holder provided with opposed openings, an elongated mold extending longitudinally in said holder and having an enlargement with portions thereof disposed in said openings, said enlargement forming a chamber and said mold also forming a tubular formation, tubular means having an inner extremity secured in said tubular formation and a fore extremity for receiving a sample of molten material for flow into said chamber, and said holder having a rear expansible and contractable extremity for accommodating and holding a front entering part of a lance.

28. A holder for use with a pair of mating sections which form a head provided with a chamber for receiving a molten material and a reduced tubular formation through which such a material may be caused to flow into the chamber, said holder being constructed of a cellulosic material and comprising a pair of channel members forming an elongated substantially tubular structure, said channel members being provided with notches which cooperate to form openings when the members are assembled whereby portions of such a head can be received in said openings whereby to assist in holding such a pair of sections assembled.

29. A device for the purpose described comprising an elongated housing having a front extremity, wall structure forming a chamber disposed in said extremity and an elongated substantially tubular formation of which a fore portion thereof extends longitudinally forward from said extremity for accommodating a tubular means having an entrance portion for receiving molten material from a supply thereof for flow into said chamber whereby to obtain a sample thereof, and means disposed in said extremity engaging portions of said wall structure forming said chamber and extending forwardly from this extremity and substantially about said tubular formation whereby to assist in holding the wall structure in said housing.

30. The device defined in claim 29, including a tubular means connected to said tubular formation and having an entrance portion which extends forwardly of said tubular formation, and said means comprises a mass of cement which also surrounds at least a portion of said entrance portion at its junction with said tubular formation.

31. A device for the purpose described comprising an elongated housing having a rear extremity for attachment to a lance and a front extremity, wall structure forming a chamber disposed in said front extremity and an elongated substantially tubular formation of which a fore portion thereof extends longitudinally forward from said front extremity, tubular means connected to said tubular formation and having an entrance portion for receiving molten material from a supply thereof for flow into said chamber whereby to obtain a sample thereof, and a mass of cement disposed in said front extremity engaging portions of said wall structure forming said chamber and extending forwardly from this extremity and substantially about said fore portion whereby to assist in holding the wall structure in said housing.

32. The device defined in claim 31, in which said entrance portion of said tubular means extends forwardly of said tubular formation, and the mass of cement also surrounds said entrance portion at least at its junction with said tubular formation.

* * * * *